United States Patent [19]
Takagi et al.

[11] 3,988,466
[45] Oct. 26, 1976

[54] PREVENTION OF GASTRIC LESIONS
[75] Inventors: Keijiro Takagi, Tokyo; Susumu Okabe, Chiba, both of Japan
[73] Assignee: Kyowa Hakko Kogyo Co., Ltd., Tokyo, Japan
[22] Filed: Mar. 6, 1975
[21] Appl. No.: 555,718

Related U.S. Application Data
[62] Division of Ser. No. 474,137, May 28, 1974, abandoned.

[30]     Foreign Application Priority Data
June 1, 1973   Japan................................ 48-61487
Dec. 17, 1973  Japan.............................. 48-139577
Dec. 17, 1973  Japan.............................. 48-139578

[52] U.S. Cl.............................. 424/274; 424/319
[51] Int. Cl.²................ A61K 31/40; A61K 31/195
[58] Field of Search................... 424/234, 274, 319

[56]          References Cited
         UNITED STATES PATENTS
3,845,210   10/1974   Soto et al........................ 424/274

*Primary Examiner*—Stanley J. Friedman
*Attorney, Agent, or Firm*—Fitzpatrick, Cella, Harper & Scinto

[57]           ABSTRACT

Gastric lesions induced by anti-inflammatory agents such as aspirin and indomethacin are prevented by the administration of amino acids. An anti-inflammatory composition comprising an anti-inflammatory agent and an amino acid is useful in the treatment of inflammation without inducing the gastric lesions.

6 Claims, No Drawings

PREVENTION OF GASTRIC LESIONS

This is a division of application Ser. No. 474,137, filed May 28, 1974, now abandoned.

BACKGROUND OF THE INVENTION

The present invention relates to the prevention of gastric lesions brought about by the administration of nonsteroidal anti-inflammatory agents. More specifically, the present invention relates to the prevention of the side effects induced by the administration of non-steroidal anti-inflammatory agents by administering at least one amino acid. The present invention also relates to anti-inflammatory compositions comprising at least one amino acid and a nonsteroidal anti-inflammatory agent.

Nonsteroidal anti-inflammatory agents, for example, aspirin, indomethacin, phenylbutazone, flufenamic acid, ibufenac, mefenamic acid and their derivatives and salts have been used widely. However, as is well known, the anti-inflammatory agents are usually toxic and often induce various side effects. Among them, gastrointestinal disorders are prominent.

On the other hand, there have been reports that amino acids, particularly, L-glutamine are effective for the prevention or treatment of certain experimental ulcers, induced artificially by, for example, stress or pylorus ligation, or chemically by histamine, reserpine or cortisone. However, such preventive or therapeautic effect of amino acids has not been reported on gastric lesions induced by nonsteroidal anti-inflammatory agents.

In an attempt to prevent the gastrointestinal disorders induced by the anti-inflammatory agents, the present inventors have conducted studies on various compounds and as the result have found that amino acids are effective for the prevention of gastric lesions caused by the administration of nonsteroidal anti-inflammatory agents, particularly, aspirin and indomethacin.

Thus, in accordance with the present invention, it has been found that amino acids can prevent gastric lesions induced by nonsteroidal anti-inflammatory agents to a considerable degree.

DETAILED DESCRIPTION OF THE INVENTION

In preventing the gastric lesions according to the present invention, at least one amino acid is administered either simultaneously with the anti-inflammatory agent or previously before or subsequently after the administration of the anti-inflammatory agents.

Various amino acids may be used in the present invention. For example, L-lysine, L-arginine, L-histidine, L-serine, L-valine, L-threonine, glycine, L-alanine, L-glutamine, D-glutamine, L-leucine, L-isoleucine, L-glutamic acid, L-asparagine, L-proline, L-hydroxyproline, L-methionine, L-phenylalanine, DL-tryptophan and their derivatives may be used. Further, pharmaceutically acceptable salts of these amino acids and their derivatives, such as acid addition salts, for example, hydrochloride, sulfate, phosphate, etc. and metal salts, for example, sodium salt, potassium salt, aluminum salt, etc. may also be used.

According to the present invention, at every administration of the anti-inflammatory agent, the amino acid is administered in an amount of at least 1 g, preferably, at least 2 g, in mixture with the anti-inflammatory agent or separately therefrom. The foregoing dosage of the amino acid is prescribed regardless of the amino acids and the kinds or doses of the anti-inflammatory agent. It is considered that when an increased dose of the anti-inflammatory agent is administered, an increased dose of the amino acid may provide good results. However, it has been found that a dose of more than 10 g of the amino acid is meaningless. For example, when the anti-inflammatory agent is aspirin and the amino acid is L-glutamine, for the single dose of aspirin, which is usually in a range of 0.3–1.0 g, L-glutamine effectively prevents gastric lesions at a dose of 2–5 g. Further, in the case of indomethacin and L-glutamine, for the usual single dose of 25–50 mg of indomethacin, an administration of 2 g of L-glutamine considerably prevents gastric lesions.

In preparing a composition containing the anti-inflammatory agent and the amino acid, the ratio of the amino acid to the anti-inflammatory agent should be determined in consideration of the foregoing. Specifically, the single dose of the amino acid of at least 1 g but not more than 10 g for any single dose of the anti-inflammatory agent is practical. The embodiment of the ratio of administration is illustrated by the specific Examples.

The amino acids may be prepared in any convenient dosage form together with the nonsteroidal anti-inflammatory agent, for example, in a compressed tablet, capsule, granule or powder according to any of the well known methods. It is to be understood, of course, that appropriate amounts of other ingredients may be incorporated into any selected dosage form so long as they do not reduce the activity of the amino acids or the anti-inflammatory agents. Such additional ingredients include starch, gelatine, agar, sugar, carboxymethylcellulose, polyvinyl alcohol, polyvinyl pyrrolidone, magnesium stearate, sodium arginate and the like.

The effect of amino acids upon the prevention of gastric lesions caused by nonsteroidal anti-inflammatory agents will be apparent from the following Experiments. It is known to those skilled in the art that the experiments performed on animals are indicative of effect in humans.

EXPERIMENT 1

Effect of L-glutamine on aspirin-induced gastric lesions in pylorus-ligated rats In this Experiment, 6 groups of male Donryu strain rats are used. The animals are fasted for 24 hours but water is allowed ad libitum. Under ether anesthesia, the pylorus is ligated according to the standard method of Shay et al.

Five groups are treated with graded doses of L-glutamine suspended in 1% carboxymethylcellulose solution by oral administration immediately after the pylorus ligation. A sixth group (control) is treated with 5 ml/kg of 1% carboxymethylcellulose solution alone. Following a control period of 10 minutes, the animals are treated with 100 mg/kg of aspirin suspended in 1% carboxymethylcellulose solution by oral administration.

After a 7-hour interval during which the animals are not allowed feed or water, the animals are killed by an overdose of ether. Ten minutes prior to the killing, the animals are treated, under ether anesthesia, with 1 ml of 5% solution of pontamine sky blue 6BX in saline (pH 7.2 adjusted with 0.5N HCl) by intravenous injection through the femoral vein.

The stomach is removed and slightly inflated by injection of 1% formalin solution through the esophagel junction. Then the stomach is maintained in 1% formalin solution for 10 minutes for fixation of the inner and outer layers of the gastric wall. The stomach is opened along the greater curvature and the length of lesions (dark blue areas against pale blue background) in the glandular portion is measured under a dissecting microscope (10x) provided with a square grid.

The results are shown in Table 1 below. The ulcer index expressed by mm indicates the mean value of the sum of the length of the lesions per animal of each group. The level of significance is calculated according to Student t-test.

Table 1

Effect of L-glutamine on aspirin-induced gastric lesions in pylorus-ligated rats

|  | Dose (mg/kg) | No. of rats | Average body weight (g) | Ulcer index (mm) | Inhibition* (%) | Level of significance |
|---|---|---|---|---|---|---|
| Control |  | 10 | 188 | 54.7±3.4 |  |  |
| L-gluta-mine | 1,000 | 12 | 189 | 3.5±1.5 | 93.6 | <0.001 |
|  | 500 | 12 | 186 | 18.0±3.1 | 67.1 | <0.001 |
|  | 250 | 12 | 182 | 15.0±3.4 | 72.6 | <0.001 |
|  | 125 | 10 | 179 | 27.9±4.7 | 49.0 | <0.001 |
|  | 62.5 | 10 | 189 | 57.6±5.6 | −5.0 | — |

*Inhibition (%) = $\frac{\text{Control ulcer index} - \text{Test ulcer index}}{\text{Control ulcer index}} \times 100$ The stomachs of three out of 12 animals treated with 1000 mg/kg of L-glutamine are quite clear and no mucosal defect is detected at all.

Although the gastric lesions preventive effect of L-glutamine may be apparent from the above table, it is noted that no such effect is observed at a dose of 62.5 mg/kg of L-glutamine.

EXPERIMENT 2

Effect of L-glutamine on indomethacin-induced gastric lesions in pylorus-ligated rats In this Experiment, 8 groups of male Donryu strain rats are used. The animals are fasted for 24 hours but water is allowed ad libitum. Under ether anesthesia, the pylorus is ligated according to the standard method of Shay et al.

Seven groups are treated with graded doses of L-glutamine suspended in 1% carboxymethylcellulose solution by oral administration immediately after the pylorus ligation. An eighth group (control) is treated with 5 ml/kg of 1% carboxymethylcellulose solution alone. Following a control period of 10 minutes, the animals are treated with 20 mg/kg of indomethacin suspended in a trace amount of Tween 80 (trade name of Atlas Chemical Industries Inc., U.S.A.) by intraperitoneal injection.

Thereafter, the animals are treated in the same manner as described in Experiment 1 and the length of lesions is measured.

The results are shown in Table 2 below.

Table 2

Effect of L-glutamine on indomethacin-induced gastric lesions in pylorus-ligated rats

|  | Dose (mg/kg) | No. of rats | Average body weight(g) | Ulcer index (mm) | Inhibition* (%) | Level of significance |
|---|---|---|---|---|---|---|
| Control |  | 22 | 150 | 12.5±3.6 |  |  |
| L-gluta-mine | 1,000 | 12 | 152 | 0.5±0.3 | 96.0 | <0.025 |
|  | 500 | 17 | 152 | 1.6±0.7 | 87.2 | <0.025 |
|  | 250 | 17 | 152 | 2.4±0.4 | 80.8 | <0.025 |
|  | 125 | 17 | 153 | 3.9±1.5 | 68.8 | <0.05 |
|  | 62.5 | 17 | 153 | 2.6±0.8 | 79.2 | <0.025 |
|  | 31.3 | 15 | 151 | 5.0±1.1 | 60.0 | >0.05 |
|  | 15.6 | 15 | 152 | 12.1±3.5 | 3.2 | >0.05 |

*Inhibition (%) = $\frac{\text{Control ulcer index} - \text{Test ulcer index}}{\text{Control ulcer index}} \times 100$ It is apparent from the above table that L-glutamine is effective for the prevention of indomethacin-induced gastric lesions in a wide range of doses (62.5 mg/kg - 1000 mg/kg). L-glutamine at a dose of 31.3 mg/kg fairly inhibits the gastric lesions but the inhibition is not significant. Further, L-glutamine at a dose of 15.6 mg/kg has no effect on the prevention of indomethacin-induced gastric lesions.

EXPERIMENT 3

Effect of various amino acids on aspirin-induced gastric lesions in pylorus-ligated rats In this Experiment, groups of male Donryu strain rats are treated in the same manner as described in Experiment 1 except that 750 mg/kg of various amino acids separately in 1% carboxymethylcellulose solution are orally administered in place of graded doses of L-glutamine; that aspirin is administered by gastric intubation in place of oral administration; and that the solution of pontamine sky blue 6 BX is injected through tail vein.

The pH values of the amino acids are also determined. The amino acids are separately dissolved or suspended in 1% carboxymethylcellulose solution at a concentration of 150 mg/ml and the pH is measured on an Hitachi pH meter (product of Hitachi Ltd., Japan).

The results are shown in Table 3 below.

Table 3

Effect of various amino acids on aspirin-induced gastric lesions in pylorus-ligated rats

| Amino acids | No. of rats | Average body weight(g) | Ulcer index (mm) | Inhibition* (%) | Level of signifi-cance | Amino acid pH |
|---|---|---|---|---|---|---|
| Control | 14 | 156 | 45.1±3.4 |  |  |  |
| L-lysine | 10 | 165 | 0.4±0.2 | 99.1 | <0.001 | 10.26 |
| L-arginine | 10 | 161 | 0.9±0.5 | 98.0 | <0.001 | 11.00 |
| L-histidine | 10 | 160 | 2.1±0.8 | 95.3 | <0.001 | 7.86 |
| L-serine | 10 | 157 | 3.0±1.0 | 93.3 | <0.001 | 6.11 |
| L-valine | 10 | 154 | 3.7±1.3 | 91.8 | <0.001 | 6.80 |
| L-threonine | 10 | 157 | 4.7±1.1 | 89.6 | <0.001 | 6.26 |
| L-glutamine | 10 | 157 | 5.5±2.0 | 87.8 | <0.001 | 6.65 |
| glycine | 10 | 162 | 6.4±1.7 | 85.8 | <0.001 | 6.12 |
| L-alanine | 10 | 157 | 6.7±1.5 | 85.1 | <0.001 | 6.45 |
| D-glutamine | 10 | 164 | 7.7±1.8 | 82.9 | <0.001 | 5.51 |
| L-leucine | 10 | 159 | 8.8±2.8 | 80.5 | <0.001 | 7.15 |

Table 3-continued

Effect of various amino acids on aspirin-induced gastric lesions in pylorus-ligated rats

| Amino acids | No. of rats | Average body weight(g) | Ulcer index (mm) | Inhibition* (%) | Level of significance | Amino acid pH |
|---|---|---|---|---|---|---|
| L-glutamic acid | 10 | 155 | 9.1±2.6 | 79.8 | <0.001 | 3.45 |
| L-asparagine | 10 | 160 | 10.0±2.2 | 77.8 | <0.001 | 5.80 |
| L-proline | 10 | 164 | 10.1±2.3 | 77.6 | <0.001 | 6.32 |
| L-isoleucine | 10 | 158 | 11.9±2.3 | 72.6 | <0.001 | 6.60 |
| L-hydroxyproline | 10 | 159 | 12.8±2.6 | 71.6 | <0.001 | 7.86 |
| L-methionine | 10 | 168 | 13.0±3.3 | 71.2 | <0.001 | 6.09 |
| L-phenylalanine | 10 | 164 | 21.5±3.7 | 52.3 | <0.001 | 6.26 |
| DL-tryptophan | 10 | 164 | 27.4±4.3 | 39.2 | <0.05 | 8.27 |
| L-aspartic acid | 10 | 157 | 37.3±6.9 | 17.3 | >0.05 | 3.33 |
| L-tyrosine | 10 | 158 | 39.3±3.0 | 12.9 | >0.05 | 7.52 |
| L-cysteine | 10 | 160 | 40.5±7.6 | 10.2 | >0.05 | 5.81 |
| L-cystine | 10 | 160 | 41.6±3.9 | 7.8 | >0.05 | 6.62 |

*Inhibition (%) = $\dfrac{\text{Control ulcer index} - \text{Test ulcer index}}{\text{Control ulcer index}} \times 100$ As is apparent from the above table, L-lysine and L-arginine prevent the aspirin-induced gastric lesions almost completely. Although L-isoleucine, L-hydroxyproline and L-methionine are effective for the prevention of the gastric lesions with high significance, the effect is found to be significantly reduced as compared with that of L-glutamine. Similarly, L-phenylalanine and DL-tryptophan show a significant inhibition of the lesions but the effect is far poorer than L-glutamine. L-aspartic acid, L-tyrosine, L-cysteine and L-cystine have no appreciable effect on the aspirin-induced gastric lesions.

Thus the effect of the specific amino acids on the prevention of aspirin-induced gastric lesions is clear from the above table. Now, such effect of amino acids is considered in view of the pH of amino acids. It is well known that the presence of acid is concerned in the induction of the gastric lesions in response to aspirin. In fact, antacids have been known to prevent aspirin-induced lesions in stomach in animals and in human beings.

In this respect, L-lysine and L-arginine, both high in alkalinity, show the best preventive effect on the gastric lesions while L-aspartic acid having the highest acidity among the tested amino acids shows no significant effect. However, it should be noted that DL-tryptophan having an alkaline pH of 8.27 has no significant preventive effect but L-glutamic acid having an acid pH of 3.45 shows good effect. L-glutamine, D-glutamine and other amino acids having the similar effect are weakly acidic or approximately neutral but L-tyrosine which similarly has a neutral pH of 7.25 shows no significant effect. Further, although L-glutamine and L-aspartic acid show almost the same pH value, their effects on the prevention of gastric lesions are much different.

From these facts, it is understood that the pH value of the specific amino acids is not critical to the gastric lesion preventive activity of amino acids. It may well be concluded that the effect of amino acids is different from that of antacids.

EXPERIMENT 4

Effect of L-glutamine on gastric secretion in pylorus-ligated rats

In this Experiment, 7 groups of male Donryu strain rats are used. After 24 hours of fasting, the pylorus of the animal is ligated in the same manner as described in Experiment 1. Six groups are treated in the same manner as described in Experiment 1 except for the injection of the solution of pontamine sky blue 6BX in saline. A seventh group (normal) is treated twice with 5 ml/kg of 1% carboxymethylcellulose solution.

After 7 hours of pylorus ligation, the animals are killed and the stomach is removed. The gastric juice is collected and the volume is measured. The gastric juice is titrated to pH 7.4 with 0.1N NaOH using an electromatic pH meter. The concentration of pepsin in the gastric juice is also determined according to Anson's hemoglobin method [Anson, M. L., J. Gen. Physiol. 22, 79 (1938)].

The results are shown in Table 4 below.

Table 4

Effect of L-glutamine on gastric secretion in pylorus-ligated rats

| | Dose (mg/kg) | No. of rats | Average body weight(g) | Gastric juice | | | |
| | | | | Volume (ml) | Titrable acidity (mEq/L) | Acid output[1] ($\mu$Eq/hr) | Pepsin Concentration (mg/ml) |
|---|---|---|---|---|---|---|---|
| Normal | | 10 | 188 | 12.3±0.4 | 120.8±2.9 | 213.3±10.7 | 25.7±0.3 |
| Control | | 10 | 183 | 12.5±0.5 | 65.1±5.7*** | 116.0±9.4*** | 31.8±1.0*** |
| L-glutamine | 1,000 | 10 | 186 | 12.2±0.3 | 139.4±3.4*** | 243.9±8.1* | 23.6±1.1 |
| | 500 | 10 | 188 | 11.9±0.4 | 127.1±4.6 | 215.5±10.3 | 25.4±0.7 |
| | 250 | 10 | 186 | 12.5±0.5 | 108.0±4.2* | 194.1±13.5 | 27.1±0.7 |
| | 125 | 10 | 187 | 12.1±0.6 | 88.9±4.8*** | 154.0±12.1** | 25.5±0.8 |
| | 62.5 | 10 | 188 | 12.3±0.5 | 56.2±3.8*** | 97.8±6.5*** | 26.3±0.5 |

*, , *indicate level of significance
*<0.05, <0.01, *<0.001
[1]acid output = volume of gastric juice × titrable acidity Table 4-continued Effect of L-glutamine on gastric secretion in pylorus-ligated rats

| Dose (mg/kg) | No. of rats | Average body weight(g) | Gastric juice | | | |
|---|---|---|---|---|---|---|
| | | | Volume (ml) | Titrable acidity (mEq/L) | Acid output[1] ($\mu$Eq/hr) | Pepsin Concentration (mg/ml) |
| hour (7) | | | | | | |

The gastric juices collected from the animals of the groups administered with 250 mg/kg or more of L-glutamine are relatively clear as compared with those collected from the animals of control group. Almost all the gastric juices collected from the animals of control group are colored brown due to hemorrhage.

It is apparent from the above table that aspirin itself does not affect the volume of gastric juice but considerably reduces the titrable acidity and acid output. It is to be noted that L-glutamine at a dose of 1000 mg/kg considerably increases the titrable acidity and acid output in spite of the presence of aspirin. No significant change is observed in such acid parameters at a dose of L-glutamine of 500 mg/kg. The acid parameters decline with the reduction of the dose of L-glutamine and are almost the same as those of the control group at a dose of 62.5 mg/kg.

On the other hand, the concentration of pepsin is increased by the administration of aspirin. It can be seen from the above table that the pepsin concentration is maintained at a normal level by the administration of L-glutamine at a wide range of doses.

From the above Experiments, the effect of amino acids on the prevention of gastric lesions induced by nonsteroidal anti-inflammatory agents may be apparent.

Further, it is confirmed by the following Experiments that amino acids have no influence on the activities of the anti-inflammatory agents per se.

EXPERIMENT A

Effect of L-glutamine on absorption of aspirin in rats

In this Experiment, 2 groups of male Wistar strain rats weighing about 280–320 g, each consisting of 12 animals are fixed in supine position. Under ether anesthesia, the carotid artery is cannulated for blood sampling. Upon recovery from the anesthesia, one group is treated with 1000 mg/kg of L-glutamine suspended in 1% carboxymethylcellulose solution and the other group (control) with 5 ml/kg of 1% carboxymethylcellulose solution alone, by oral administration. Ten minutes after the treatment, the animals are orally administered 100 mg/kg of aspirin suspended in 1% carboxymethylcellulose solution. The same treatments are applied also to 2 groups of pylorus-ligated rats, each consisting of 5 animals.

After the administration of aspirin, approximately 50 $\mu$l of blood is taken from each animal with a glass capillary at the time indicated. The blood sample is centrifuged at 8,000 r.p.m. for 5 minutes and 20 $\mu$l of plasma is collected for the measurement of salicylate concentration. Salicylate concentration of plasma is determined according to the method of Lever & Powell [Lever, M. and Powell, J. C.: Biochem. Med., 7, 203 (1973)].

The results are shown in Table 5 below.

Table 5

| | | No. of rats | Plasma salicylate level after administration of asprin | | | | | | | |
|---|---|---|---|---|---|---|---|---|---|---|
| | | | Plasma salicylate concentration ($\mu$g/ml) | | | | | | | |
| | | | 5(min) | 10 | 20 | 40 | 100 | 160 | 300 | 420 |
| Normal rats | Control | 12 | 132±11 | 164±9 | 178±11 | 187±11 | 181±10 | 174±11 | 157±10 | 139±13 |
| | L-glutamine (1000 mg/kg) | 12 | 82±13 | 124±12 | 174±13 | 205±12 | 204±10 | 195±10 | 174±7 | 161±8 |
| Pylorus-ligated rats | Control | 5 | 20±4 | 44±3 | 63±5 | 83±9 | 125±11 | 142±8 | 177±15 | 201±19 |
| | L-glutamine (1000 mg/kg) | 5 | 19±2 | 52±3 | 89±7 | 127±11 | 174±13 | 195±11 | 231±12 | 239±24 |

EXPERIMENT B

Effect of L-glutamine on antipyretic activity of aspirin in rats

In this Experiment, male Wistar strain rats weighing about 90–100 g are treated with 2.5 ml/rat of a suspension of yeast (Brewers Yeast, product of Nutritional Biochem. Co., U.S.A.) in physiological saline (concentration: 250 mg/ml), by subcutaneous injection in the back, according to the method of Gleen et al [Gleen, E. M. et al: J. Pharma. Exp. Therp., 155, 157 (1967)]. The animals are then fasted. The animals showing an increased rectal temperature of 38° C or more after 17 hours are selected for use in experiment. The animals are treated with a solution of aspirin and/or a suspension of L-glutamine in 1% carboxymethylcellulose solution in a specified amount by oral administration. As a control, one group is treated with 105 ml of 1% carboxymethylcellulose solution alone. After the treatment, the rectal temperature is measured at the time indicated. The results are shown in Table 6 below.

Table 6

| Treatment | No. of rats | Rectal temperature (° C) Time after administration (hour) | | | | |
|---|---|---|---|---|---|---|
| | | 0 | 1 | 2 | 4 | 6 |
| Control | 37 | 38.2±0.1 | 38.1±0.1 | 37.9±0.2 | 37.8±0.2 | 38.0±0.1 |
| Aspirin (200 mg/kg) | 37 | 38.4±0.1 | 37.9±0.1 | 36.7±0.2 | 36.6±0.1 | 36.9±0.2 |
| Aspirin (200 mg/kg) + L-glutamine (500 mg/kg) | 37 | 38.4±0.2 | 37.7±0.1 | 36.5±0.2 | 36.5±0.2 | 37.0±0.2 |
| Aspirin (200 mg/kg) + L-glutamine (1000 mg/kg) | 37 | 38.4±0.1 | 37.9±0.1 | 36.3±0.2 | 36.4±0.2 | 36.9±0.1 |
| L-glutamine (1000 mg/kg) | 37 | 38.6±0.2 | 38.5±0.2 | 38.2±0.3 | 38.1±0.4 | 38.2±0.3 |

EXPERIMENT C

Effect of L-glutamine on analgesic activity of aspirin in mice

In this Experiment, 3 groups of male dd strain mice weighing 19–21 g are used.

A first group of the animals is treated with 300 mg/kg of aspirin suspended in 1% carboxymethylcellulose solution alone and a second group with the same amount of aspirin in combination with 1000 mg/kg of L-glutamine suspended in 1% carboxymethylcellulose solution, by oral administration. As a control, the third group is treated only with 1% carboxymethylcellulose solution. After a control period of one hour, the animals are treated with 0.2 ml of 0.7% acetic acid solution in physiological saline by intraperitoneal injection, according to the method of Koster et al. [Koster, R. et al: Fed. Proc., 18, 412 (1959)]. Starting 10 minutes after the administration of acetic acid, the number of writhing reaction occurred in 10 minutes is counted. The results are shown in Table 7 below.

Table 7

Effect of aspirin and aspirin plus L-glutamine on acetic acid-induced writhing response in mice

| Treatment | No. of rats | Writhing response | |
|---|---|---|---|
| | | Number | Suppression ratio (%) |
| Control | 37 | 21±2 | |
| Aspirin (300 mg/kg) | 39 | 10±1 | 52.7 |
| Aspirin (300 mg/kg) + L-glutamine (1000 mg/kg) | 38 | 13±2 | 38.1 |

EXPERIMENT D

Effect of L-glutamine on anti-inflammatory activity of aspirin in rats

In this Experiment, 5 groups of male Donryu strain rats weighing 90–100 g are treated with specified amount of aspirin and/or L-glutamine, respectively suspended in 1% carboxymethylcellulose solution, by oral administration. As a control, a sixth group is treated with 1% carboxymethylcellulose solution. After one hour, the animals are treated with a phlogistic agent of 0.1 ml of 1% carrageenin solution by subcutaneous injection in a hind paw, according to the method of Yamasaki et al. [Yamasaki, H. et al: Folia Pharm. Jap., 63, 302 (1967)]. Swelling of the paw is measured 5 hours after the administration of the phlogistic agent. The results are shown in Table 8 below.

Table 8

Effect of aspirin and/or L-glutamine on carageenin-induced paw edema in rats

| Treatment | | No. of rats | Swelling ratio (%) | Suppression ratio (%) |
|---|---|---|---|---|
| Control | | 20 | 123.9±7.0 | |
| Aspirin (200 mg/kg) | | 20 | 88.5±4.2 | 28.6 |
| Aspirin (200 mg/kg) | + L-glutamine (1000 mg/kg) | 20 | 86.3±8.5 | 30.3 |
| Aspirin (400 mg/kg) | | 20 | 65.6±5.0 | 47.1 |
| Aspirin (400 mg/kg) | + L-glutamine (1000 mg/kg) | 20 | 53.5±6.8 | 56.8 |
| L-glutamine (1000 mg/kg) | | 10 | 117.2±4.7 | 5.4 |

It is apparent from the above table 5 that when L-glutamine is administered together with aspirin, substantially the same plasma salicylate levels as, or even higher ones than, those obtained by the administration of aspirin alone, are maintained. This means that the presence of L-glutamine does not inhibit the absorption of aspirin.

Also it is apparent from the above Tables 6 – 8 that the antipyretic, analgesic and anti-inflammatory activities of aspirin are not substantially influenced by the presence of L-glutamine.

Thus, it may be demonstrated that the administration of amino acids on the occasion of the administration of an anti-inflammatory agent markedly prevents the development of gastric lesions induced by the anti-inflammatory agent, while in no way inhibiting the pharmacological activities of anti-inflammatory agent.

The present invention is further illustrated by the following representative Examples.

EXAMPLE 1

150 g of powdered aspirin and 25 g of dry starch are mixed and made into granules of under 16 meshes according to a known method. Separately, 18 g of polyvinyl pyrrolidone is dissolved in 50 g of distilled water. To the solution is added 600 g of L-glutamine and the mixture is similarly made into granules of under 16 meshes. Two kinds of granules thus prepared and 8 g of magnesium stearate are homogeneously mixed together and compressed into tablets of 455 mg each.

EXAMPLE 2

45 g of polyvinyl pyrrolidone is dissolved in 125 g of distilled water. To the solution is added 1500 g of L-lysine and the mixture is made into granules of under 16 meshes. The resulting granules and 350 g of granules consisting of powdered aspirin and dry starch prepared in the same manner as in Example 1 are mixed and 5 g of magnesium stearate is added thereto. The mixture is compressed into tablets of 625 mg each.

EXAMPLE 3

90 g of L-isoleucine, 102 g of L-leucine, 112 g of L-lysine hydrochloride, 60 g of L-phenylalanine, 90 g of L-methionine, 60 g of L-threonine, 30 g of L-tryptophan, 90 g of L-valine, 134 g of L-arginine hydrochloride, 65 g of L-histidine hydrochloride and 60 g of dry starch are mixed and made into granules of under 16 meshes. Separately, 200 g of powdered aspirin and 30 g of dry starch are mixed and made into granules of under 16 meshes. The two kinds of granules prepared above are mixed and 7 g of magnesium stearate is added thereto. The mixture is compressed into tablets of 500 mg each.

EXAMPLE 4

6 g of powdered indomethacin, 500 g of L-glutamine and 50 g of dry starch are mixed and to the mixture is added a solution of 18 g of polyvinyl pyrrolidone in 55 g of distilled water. The resulting mixture is made into granules of under 16 meshes. The granules are mixed with 30 g of cellulose crystallites and 2 g of magnesium stearate and the mixture is compressed into tablets of 300 mg each.

EXAMPLE 5

12 g of indomethacin, 1,000 g of L-glutamine and 100 g of dry starch are mixed and to the mixture is added a solution of 33 g of polyvinyl pyrrolidone in 100 g of distilled water and the resulting mixture is made into granules of under 20 meshes. The granules are mixed with 100 g of milk casein, 100 g of starch and 5 g of magnesium stearate and the mixture is filled into capsules each containing 5 mg of indomethacine.

What is claimed is:

1. An anti-inflammatory composition which comprises in single oral dose form from 25 mg to 50 mg of indomethacin and from 1g to 10g of at least one amino acid selected from the group consisting of L-lysine, L-arginine, L-histidine, L-serine, L-valine, L-threonine, glycine, L-alanine, L-glutamine, D-glutamine, L-leucine, L-isoleucine, L-glutamic acid, L-asparagine, L-proline, L-hydroxyproline, L-methionine, L-phenylalanine, DL-tryptophan, or a pharmaceutically acceptable non-toxic salt thereof.

2. Composition according to claim 1 wherein said amino acid is L-glutamine acid.

3. A method of preventing gastric lesions induced by the administration of an effective dose of indomethacin which comprises orally administering from 1g to 10g per 25 mg to 50 mg of indomethacin of at least one amino acid selected from the group consisting of L-lysine, L-arginine, L-histidine, L-serine, L-valine, L-threonine, glycine, L-alanine, L-glutamine, D-glutamine, L-leucine, L-isoleucine, L-glutamic acid, L-asparagine, L-proline, L-hydroxyproline, L-methionine, L-phenylalanine, DL-tryptophan, or a pharmaceutically acceptable non-toxic salt thereof.

4. A method according to claim 3 wherein said indomethacin and amino acid are administered in combination dosage form.

5. A method according to claim 1 wherein said indomethacin and amino acid are administered in separate dosage form.

6. A method according to claim 3 wherein said amino acid is L-glutamine.

* * * * *

UNITED STATES PATENT OFFICE
CERTIFICATE OF CORRECTION

Patent No. 3,988,466      Dated October 26, 1976

Inventor(s) Keijiro Takagi, et al

It is certified that error appears in the above-identified patent and that said Letters Patent are hereby corrected as shown below:

Column 5, line 10 in Table 3 "72.6" should be --73.6--;

Columns 5 and 6, under Table 4, the last line should read:

--$^1$acid output= $\dfrac{\text{volume of gastric juice} \times \text{titrable acidity}}{\text{hour}}$ (7)

Columns 7 and 8, "Table 4 - continued and the first 12 lines of such Table" should be deleted.

Column 8, line 65, "105" should be --1.5--

Column 12, line 22, "acid" (second occurrence) should be deleted.

Signed and Sealed this

Twenty-second Day of February 1977

[SEAL]

Attest:

RUTH C. MASON
Attesting Officer

C. MARSHALL DANN
Commissioner of Patents and Trademarks